(12) United States Patent
Igarashi et al.

(10) Patent No.: US 6,800,607 B2
(45) Date of Patent: Oct. 5, 2004

(54) MODIFIED BDNF

(75) Inventors: Rie Igarashi, Kawasaki (JP); Yutaka Mizushima, Tokyo-to (JP); Mutsuo Taiji, Takatsuki (JP); Chikao Nakayama, Sanda (JP); Hiroshi Noguchi, Kawanishi (JP)

(73) Assignee: LTT Bio-Pharma Co., Ltd., Tokyo-to (JP)

( * ) Notice: Subject to any disclaimer, the term of this patent is extended or adjusted under 35 U.S.C. 154(b) by 0 days.

(21) Appl. No.: 10/220,315

(22) PCT Filed: Feb. 26, 2001

(86) PCT No.: PCT/JP01/01422

§ 371 (c)(1),
(2), (4) Date: Aug. 29, 2002

(87) PCT Pub. No.: WO01/64742

PCT Pub. Date: Sep. 7, 2001

(65) Prior Publication Data

US 2003/0073631 A1 Apr. 17, 2003

(30) Foreign Application Priority Data

Feb. 29, 2000 (JP) ........................................ 2000-053581

(51) Int. Cl.⁷ .............................................. A61K 38/16
(52) U.S. Cl. ..................... 514/7; 514/2; 514/7; 514/12; 530/324; 530/350; 530/416
(58) Field of Search ................... 514/7, 2, 12; 530/324, 530/350, 416; 424/198.1, 184.1

(56) References Cited

U.S. PATENT DOCUMENTS 6,391,312 B1    5/2002   Kishino et al.

FOREIGN PATENT DOCUMENTS

| JP | 3-163100 A | 7/1991 |
| JP | 2679852 | 8/1997 |
| JP | 2718809 | 11/1997 |
| WO | 98/32458 A | 7/1998 |

OTHER PUBLICATIONS

Taiji M. et al., BDNF: A Novel Hypoglycemic Agent Acting Central Nervous System, Cell vol. 31, pp. 488–491, No. 12 (1999).
Sakane et al., Reduction of the Plasma Clearance of Brain–Derived Neurotrophic Factor (BDNF) : Carboxyl–Directed Pegylation, Drug Delivery System, vol. 13, pp. 173–178, No. 3 (1998).

*Primary Examiner*—Christopher R. Tate
*Assistant Examiner*—B. Dell Chism
(74) *Attorney, Agent, or Firm*—Birch, Stewart, Kolasch & Birch, LLP

(57) ABSTRACT

Modified BDNF having improved pharmacological activities, pharmacokinetics and physical properties can be obtained by modifying BDNF with a 1-acyl-glycerol derivative. This BDNF being modified with a 1-acyl-glycerol derivative of the present invention has more efficacious and more excellent pharmacokinetic properties with retaining the useful effects being characteristic to BDNF which are useful as remedies for neurodegenerative diseases and diabetes mellitus, and hence, it is particularly useful as a therapeutic agent for treatment of type 2 diabetes mellitus.

13 Claims, 2 Drawing Sheets

MODIFIED BDNF

This application is the national phase under 35 U.S.C. § 371 of PCT International Application No. PCT/JP01/01422 which has an International filing date of Feb. 26, 2001, which designated the United States of America.

TECHNICAL FIELD

The present invention relates to a brain-derived neurotrophic factor being modified with a 1-acyl-glycerol derivative. In addition, the present invention also relates to an agent for treatment of type 2 diabetes mellitus, which comprises as the active ingredient a brain-derived neurotrophic factor being modified with a 1-acyl-glycerol-derivative.

BACKGROUND ART

One of the neurotrophic factors, a brain-derived neurotrophic factor (hereinafter, occasionally referred to as BDNF), is a protein, which is provided from target cells or neurons and glial cells and Schwann cells in the living body, and shows activities to maintain the survival and differentiation of neurons. BDNF has been known to act as a specific ligand of receptor (trkB), which is a product of p75 and trk genes (cf., Takeshi NONOMURA, Hiroshi HATANAKA; Jikken Igaku, vol. 13, p. 376 (1995)).

BDNF has been known as a therapeutic agent for treatment of neurodegenerative diseases (e.g., ALS) or diabetic peripheral neuropathy (cf., A. P. Mizisin, et al., Journal of Neuropathology and Experimental Neurology, vol.56, p. 1290 (1997)).

In addition, WO 98/32458 discloses that BDNF is useful as a therapeutic agent for treatment of diabetic mellitus.

Since BDNF is a useful protein exhibiting the above mentioned various functions, it has been desired to develop a compound with more efficacious and more excellent pharmacokinetics with retaining inherent activities of BDNF.

There has been tried to improve the physical properties and activities of proteins with maintaining their functions by modifications. For example, JP 2679852 and JP 2718809 disclose common techniques of modifying physiologically active proteins with lecithin or lysolecithin, specifically modification of superoxide dismutase (SOD). However, there is no specific disclosure of modifying BDNF, which is a useful protein exhibiting various functions.

DISCLOSURE OF INVENTION

An object of the present invention is to provide a compound being more efficacious with retaining inherent activities of BDNF and further having an excellent pharmacokinetics.

The present inventors have found that the pharmacological activities, pharmacokinetics and physical properties of BDNF are improved by modifying BDNF with a 1-acyl-glycerol derivative, and have accomplished the present invention.

More particularly, the present invention relates to the following:

(1) A BDNF being modified with a 1-acyl-glycerol derivative:

(2) A modified BDNF according to the above (1), which is the compound of the formula (1):

$$A(X-B)_m \quad (1)$$

wherein A is a residue of brain-derived neurotrophic factor,
B is a residue of a 1-acyl-glycerol derivative having a hydroxyl group at the 2-position of the glycerol moiety, which is prepared by removing a hydrogen atom from the hydroxyl group,
X is a chemical cross-linkage, and
m is an average number of the introduction and is not less than about 0.5;

(3) A modified BDNF according to the above (2), wherein X is a group of the formula (2):

wherein $R^1$ is an alkylene group,
or a group of the formula (3):

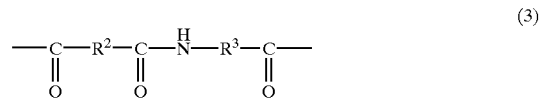

wherein $R^2$ and $R^3$ are independently an alkylene group;

(4) A modified BDNF according to the above (2), wherein the 1-acyl-glycerol derivative is 1-acyl-glycero-3-phosphoryl choline, 1-acyl-glycero-3-phosphoryl serine, or 1-acyl-grycero-3-phosphoryl ethylamine;

(5) A modified BDNF according to the above (2), wherein B is a 1-acyl-glycero-3-phosphoryl choline residue of the formula (4):

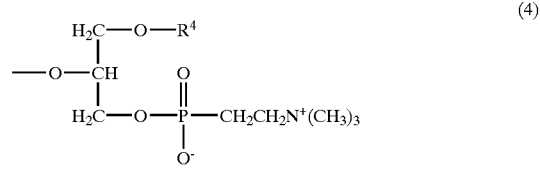

wherein $R^4$ is an acyl group,
a 1-acyl-glycero-3-phosphoryl serine residue of the formula (5):

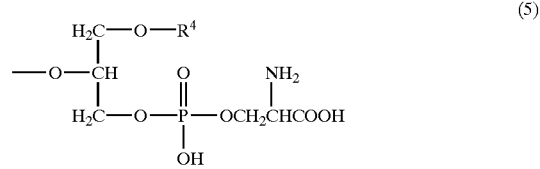

wherein $R^4$ is an acyl group,
or a 1-acyl-glycero-phosphoryl ethylamine residue of the formula (6):

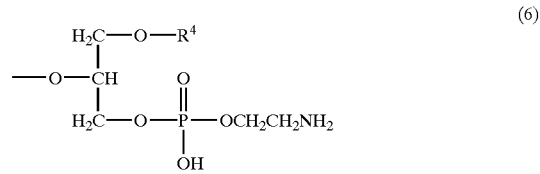

wherein $R^4$ is an acyl group;
(6) A modified BDNF according to the above (2) or (3), wherein B is a group of the formula (4):

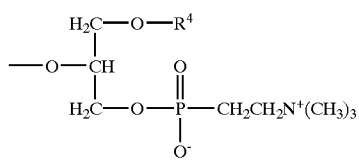 (4)

wherein R⁴ is an acyl group;

(7) A modified BDNF according to any one of the above (2), (3), (4), (5) and (6), wherein the acyl group is an alkanoyl group having 8 to 30 carbon atoms;
(8) A modified BDNF according to any one of the above (2), (3), (4), (5), (6) and (7), wherein the acyl group is palmitoyl group;
(9) A modified BDNF according to any one of the above (2), (3), (4), (5), (6), (7) and (8), wherein m is in the range of from about 1 to about 6;
(10) A modified BDNF according to any one of the above (2), (3), (4), (5), (6), (7), (8) and (9), wherein X is a group of the formula (2):

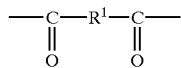 (2)

wherein R¹ is an alkylene group;
(11) A modified BDNF according to the above (10), wherein R¹ is a straight chain alkylene group having 2 to 10 carbon atoms;
(12) A modified BDNF according to the above (10), wherein R¹ is trimethylene;
(13) A modified BDNF of the formula (7):

A(X—B)$_n$ (7)

wherein A is a residue of brain-derived neurotrophic factor,
B is a residue of a 1-acyl-glycerol derivative having a hydroxyl group at the 2-position of the glycerol moiety, which is prepared by removing a hydrogen atom from the hydroxyl group,
X is a chemical cross-linkage, and
n is an integer of 1 or more;
(14) A modified BDNF according to the above (13), wherein X is a group of the formula (2):

 (2)

wherein R¹ is an alkylene group, or
or a group of the formula (3):

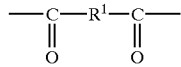 (3)

wherein R² and R³ are independently an alkylene group;
(15) A modified BDNF according to the above (13), wherein B is a 1-acyl-glycero-3-phosphoryl choline residue of the formula (4):

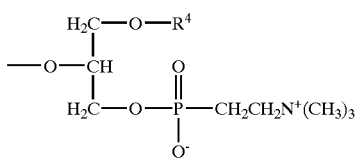 (4)

wherein R⁴ is an acyl group,
a 1-acyl-glycero-3-phosphoryl serine residue of the formula (5):

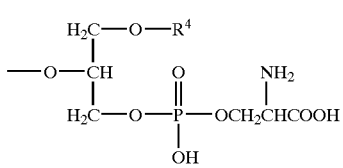 (5)

wherein R⁴ is an acyl group,
or a 1-acyl-glycero-phosphoryl ethylamine residue of the formula (6):

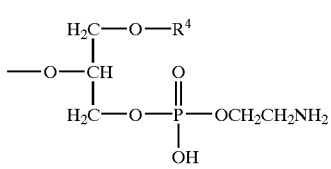 (6)

wherein R⁴ is an acyl group;
(16) A modified BDNF according to the above (13) or (14), wherein B is a group of the formula (4):

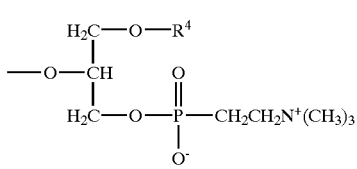 (4)

wherein R⁴ is an acyl group;
(15) A therapeutic agent for treatment of type 2 diabetes mellitus, which comprises as the active ingredient a BDNF being modified with a 1-acyl-glycerol derivative;
(16) A therapeutic agent for treatment of type 2 diabetes mellitus comprising as the active ingredient a modified BDNF according to the above (15), which is a compound of the formula (1):

A (X—B)$_m$ (1)

wherein A is a residue of brain-derived neurotrophic factor,
B is a residue of a 1-acyl-glycerol derivative having a hydroxyl group at the 2-position of the glycerol moiety, which is prepared by removing a hydrogen atom from the hydroxyl group,
X is a chemical cross-linkage, and
m is an average number of the introduction and is not less than about 0.5;
(17) A therapeutic agent for treatment of type 2 diabetes mellitus comprising as the active ingredient a modified BDNF according to the above (16), wherein X is a group of the formula (2):

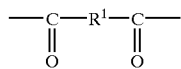

(2)

wherein $R^1$ is an alkylene group,
or a group of the formula (3):

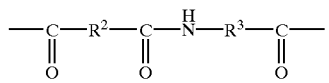

(3)

wherein $R^2$ and $R^3$ are independently an alkylene group;

(18) A therapeutic agent for treatment of type 2 diabetes mellitus comprising as the active ingredient a modified BDNF according to the above (16), wherein the 1-acyl-glycerol derivative is 1-acyl-glycero-3-phosphoryl choline, 1-acyl-glycero-3-phosphoryl serine, or 1-acyl-grycero-3-phosphoryl ethylamine;

(19) A therapeutic agent for treatment of type 2 diabetes mellitus comprising as the active ingredient a modified BDNF according to the above (16), wherein B is a 1-acyl-glycero-3-phosphoryl choline residue

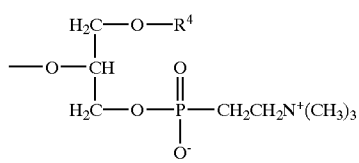

(4)

wherein $R^4$ is an acyl group,
a 1-acyl-glycero-3-phosphoryl serine residue of the formula (5):

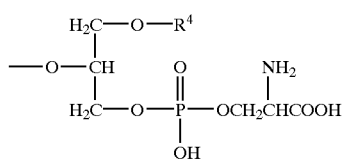

(5)

wherein $R^4$ is an acyl group,
or a 1-acyl-glycero-phosphoryl ethylamine residue of the formula (6):

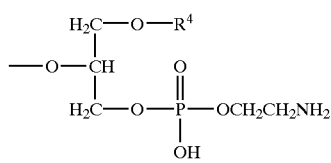

(6)

wherein $R^4$ is an acyl group;

(20) A therapeutic agent for treatment of type 2 diabetes mellitus comprising as the active ingredient a modified BDNF according to the above (16) or (17), wherein B is a group of the formula (4):

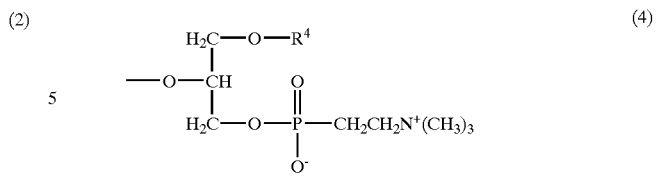

(4)

wherein $R^4$ is an acyl group;

(21) A therapeutic agent for treatment of type 2 diabetes mellitus comprising as the active ingredient a modified BDNF according to any one of the above (16), (17), (18), (19) and (20), wherein the acyl group is an alkanoyl group having 8 to 30 carbon atoms;

(22) A therapeutic agent for treatment of type 2 diabetes mellitus comprising as the active ingredient a modified BDNF according to any one of the above (16), (17), (18), (19), (20) and (21), wherein the acyl group is palmitoyl group;

(23) A therapeutic agent for treatment of type 2 diabetes mellitus comprising as the active ingredient a modified BDNF according to any one of the above (16), (17), (18), (19), (20), (21) and (22), wherein m is in the range of from about 1 to about 6;

(24) A therapeutic agent for treatment of type 2 diabetes mellitus comprising as the active ingredient a modified BDNF according to any one of the above (16), (17), (18), (19), (20), (21), (22) and (23), wherein X is a group of the formula (2):

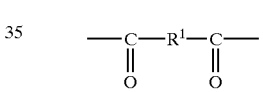

(2)

wherein $R^1$ is an alkylene group;

(25) A therapeutic agent for treatment of type 2 diabetes mellitus comprising as the active ingredient a modified BDNF according to the above (24), wherein $R^1$ is a straight chain alkylene group having 2 to 10 carbon atoms;

(26) A therapeutic agent for treatment of type 2 diabetes mellitus comprising as the active ingredient a modified BDNF according to the above (25), wherein $R^1$ is trimethylene;

(27) A therapeutic agent for treatment of type 2 diabetes mellitus comprising as the active ingredient a modified BDNF, which is the compound of the formula (7):

$A(X-B)_n$ (7)

wherein A is a residue of a brain-derived neurotrophic factor,
B is a residue of a 1-acyl-glycerol derivative having a hydroxyl group at the 2-position of the glycerol moiety, which is prepared by removing a hydrogen atom from the hydroxyl group,
X is a chemical cross-linkage, and
n is an integer of 1 or more;

(28) A therapeutic agent for treatment of type 2 diabetes mellitus comprising as the active ingredient a modified BDNF according to the above (27), wherein X is a group of the formula (2):

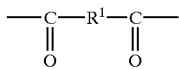 (2)

wherein R$^1$ is an alkylene group, or a group of the formula (3):

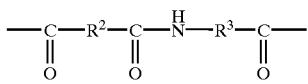 (3)

wherein R$^2$ and R$^3$ are independently an alkylene group.

(29) A therapeutic agent for treatment of type 2 diabetes mellitus comprising as the active ingredient a modified BDNF according to the above (27), wherein B is a 1-acyl-glycero-3-phosphoryl choline residue of the formula (4):

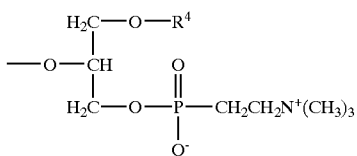 (4)

wherein R$^4$ is an acyl group, a 1-acyl-glycero-3-phosphoryl serine residue of the formula (5):

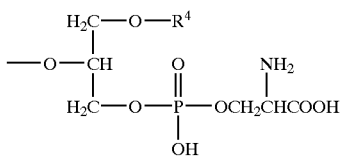 (5)

wherein R$^4$ is an acyl group, or a 1-acyl-glycero-phosphoryl ethylamine residue of the formula (6):

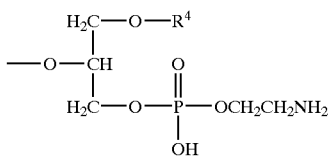 (6)

wherein R$^4$ is an acyl group;

(30) A therapeutic agent for treatment of type 2 diabetes mellitus comprising as the active ingredient a modified BDNF according to the above (27) or (28), wherein B is a group of the formula (4):

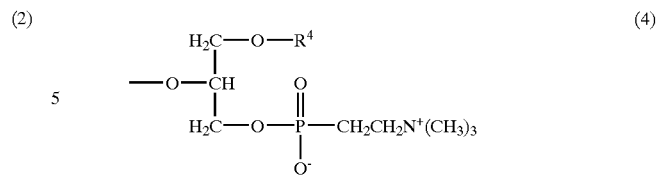 (4)

wherein R$^4$ is an acyl group.

BEST MODE FOR CARRYING OUT THE INVENTION

Figure 1:
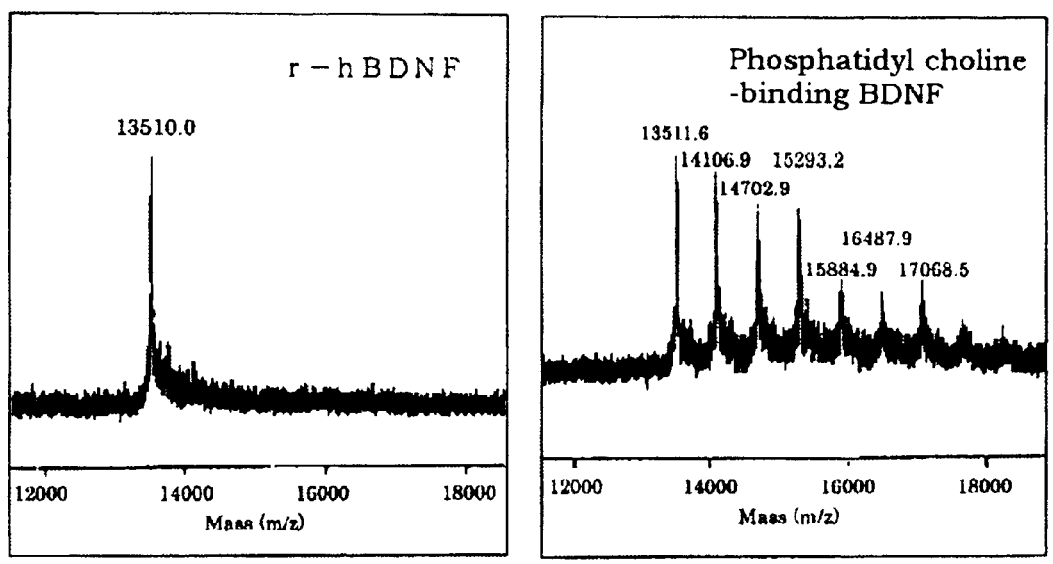
FIG. 1 indicates a spectrum pattern of time-of-flight mass spectrometry (TOF-MALDI MS) of the lecithinized brain-derived neurotrophic factor obtained in Example 1 and a brain-derived neurotrophic factor.

A brain-derived neurotrophic factor being modified with a 1-acyl-glycerol derivative of the present invention (hereinafter, occasionally abbreviated as a modified BDNF) can be used as a therapeutic agent for treatment of nervous system disorders and diseases, or treatment of diabetes mellitus. More particularly, the brain-derived neurotrophic factor being modified with a 1-acyl-glycerol derivative of the present invention can be administered to patients having nervous system injured by wound, surgery, ischemia, infection, metabolic diseases, malnutrition, malignant tumor, or toxic drug, etc. Especially, it can be used in the treatment of conditions wherein sensory neurons or retinal ganglion cells are injured. More especially, the modified BDNF of the present invention can be used in the treatment of congenital conditions or neurodegenerative diseases, for example, Alzheimer's disease, Parkinson's disease (the symptoms of Parkinson's disease may be caused by the degeneration of dopaminergic neuron), Parkinson-Plus syndromes (e.g., progressive spranuclear palsy (Steele-Richardson-Olszewski syndromes), olivopontocerebellar atrophy (OPCA), Shy-Drager syndromes (Multiple Systems Atrophy), and Parkinson dementia complex of Guam), and Huntington's chorea, but are not limited thereto. Further, the present modified BDNF can be used in the treatment of sensory nerve dysfunction and congenital diseases or neurodegenerative diseases being associated with degenerative of retina. In addition, the present modified BDNF can be used in the treatment of inherited convulsive paraplegia associated with retina degeneration (Kjellin and Barnard-Scholz syndromes), retinitis pigmentosa, Stargardt disease, Usher syndromes (retinitis pigmentosa accompanied by congenital hearing loss) and Refsum syndrome (retinitis pigmentosa, congenital hearing loss, and polyneuropathy).

The present modified BDNF can also be used in order to accelerate the recovery of a patient of diabetic neuropathy or multiple mononeuropathy. Further, the present modified BDNF can also be used as a therapeutic agent for treatment of diabetes mellitus, especially type 2 diabetes mellitus having a hyperglycemia due to insulin dysfunction or insulin resistance, etc.

In addition, the present modified BDNF can be used as an agent for ameliorating insulin dysfunction or insulin resistance, or an agent for treating or ameliorating hyperglycemia accompanied by reduction or failure of insulin secretion, or an agent for treating or ameliorating hyperlipemia, or an agent for treating or ameliorating hyperinsulinemia.

The groups of the formula (1), the formula (2), the formula (3), the formula (4), the formula (5) and the formula (6) are explained in more detail.

The residue of a brain-derived neurotrophic factor as represented by A means a residue being prepared by removing m or n numbers of hydroxyl groups or hydrogen atoms to which a group of $(X-B)_m$ or $(X-B)_n$ bound, from the functional groups such as carboxyl groups and amino groups of an amino acid (e.g., lysine residue) of BDNF.

The average number of the introduction of modifying groups means the average number of modifying groups being introduced into one molecule of BDNF, and is not less than 0.5, preferably about 1 or more, more preferably in the range of about 1 to about 10, especially in the range of about 1 to about 6. Most preferably, it is in the range of about 2 to about 4.

The integer of 1 or more for n is, for example, an integer of 1 to 10, preferably an integer of 1 to 6, more preferably an integer of 2 to 4.

The alkylene group includes a straight chain or branched chain alkylene group having 1 to 24 carbon atoms, preferably a straight chain alkylene group having 2 to 10 carbon atoms, for example, ethylene, trimethylene, tetramethylene, pentamethylene, hexamethylene, heptamethylene, octamethylene, nonamethylene, decamethylene, etc.

The acyl group includes, for example, an alkanoyl group, an alkenoyl group, an aroyl group, a substituted aroyl group, etc.

The alkanoyl group includes an alkanoyl group having 8 to 30 carbon atoms, for example, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, eicosanoyl, heneicosanoyl, tricosanoyl, tetracosanoyl, pentacosanoyl, hexacosanoyl, heptacosanoyl, octacosanoyl, nonacosanoyl, triacontanoyl, etc., and preferably an alkanoyl group having 14 to 22 carbon atoms such as tetradecanoyl, pentadecanoyl, hexadecanoyl, heptadecanoyl, octadecanoyl, nonadecanoyl, eicosanoyl, heneicosanoyl, etc.

The aroyl group includes an aroyl group having 7 to 11 carbon atoms, for example, benzoyl group, naphthoyl group, etc.

The alkenoyl group includes an alkenoyl group having 8 to 30 carbon atoms, for example, oleoyl, linoleoyl, arachidonoyl, etc.

The substituted aroyl group includes an aroyl group being substituted by an alkyl group, a halogen atom, an alkoxy group, a hydroxyl group, a nitro group, etc., for example, 4-methylbenzoyl, 2-methylbenzoyl, 4-fluorobenzoyl, 2-fluorobenzoyl, 4-chlorobenzoyl, 3-chlorobenzoyl, 2-chlorobenzoyl, 4-methoxybenzoyl, 3-methoxybenzoyl, 2-methoxybenzoyl, 4-hydroxybenzoyl, 3-nitrobenzoyl, etc.

The alkyl group includes a lower alkyl group having 1 to 6 carbon atoms, etc., for example, methyl, ethyl, propyl, butyl, pentyl, hexyl, 2-methylpropyl, etc.

The halogen atom is fluorine atom, chlorine atom, bromine atom, and iodine atom.

The alkoxy group includes a lower alkoxy group having 1 to 6 carbon atoms, etc., for example, methoxy, ethoxy, propyloxy, butyloxy, pentyloxy, hexyloxy, 2-methylpropyloxy, etc.

The chemical cross-linkage for X is a chemical cross-linkage consisting of an organic group combining A and B after the chemical cross-linking reaction. One end of the chemical cross-linkage is preferably bound to the 1-acyl-glycerol derivative via an ester bond. The other end of the chemical cross-linkage is directly bound to a functional group such as an amino group or a carboxyl group of the brain-derived neurotrophic factor. The chemical cross-linkage preferably has a carboxyl group, an amino group, a hydroxyl group, an imino group, etc. as a functional group. In addition, the chemical cross-linkage may optionally has two or more functional groups, and one of the functional groups is bound to the 1-acyl-glycerol derivative and other functional group is bound to a functional group of the brain-derived neurotrophic factor. The chemical cross-linkage may further intervene between other functional groups. Preferable chemical cross-linkage is, for example, a group of the formula (2):

(2)

wherein $R^1$ is an alkylene group,
a group of the formula (3):

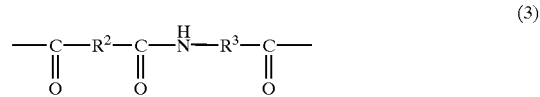

(3)

wherein $R^2$ and $R^3$ are independently an alkylene group, and the like. More preferable chemical cross-linkage is a group of the formula (2':

(2')

wherein $R^{1\,'}$ is a $C_2$–$C_{10}$ alkylene group.

In the integer of 1 or more for n, preferable integer is in the range of 1 to 10, and more preferable integer is in the range of 1 to 5.

The brain-derived neurotrophic factor (BDNF) of the present invention includes modified ones prepared by deletion of a part of amino acid sequence, or a substitution by other amino acid(s), or an addition of a part of other amino acid sequence, or ones having one or more amino acids bound at the N-terminus and/or the C-terminus, or ones wherein the sugar chain is deleted or substituted, as far as they exhibit substantially the same activity as naturally occurred brain-derived neurotrophic factor.

The BDNF used in the present invention can be prepared by various methods, for example, by cultivating a primary culture cell or an established cell line that can produce the neurotrophic factor, and isolating and purifying it from the culture medium thereof (e.g., culture supernatant, cultured cells). Moreover, a recombinant neurotrophic factor can be obtained by a conventional gene engineering technique, e.g., by inserting a gene encoding a BDNF into a suitable vector, transforming a suitable host with the recombinant vector, and isolating from a culture supernatant of the resulting transformant. The host cells to be used in the above process are not limited, and may be any conventional host cells which have been used in a gene engineering technique, for example, *Escherichia coli, Bacillus subtilis*, yeasts, mold fungi, plant cells or animal cells. For example, when a conventional gene engineering technique is employed, BDNF is prepared by inserting a gene encoding BDNF into a suitable vector, transforming a suitable host with the recombinant vector, and isolating it from a culture supernatant of the resulting transformant (cf., Prof. Natl. Acad. Sci. USA, vol. 88, p. 961 (1991); Biochem. Biophys. Res. Commun., vol. 186, p. 1533 (1992)). The gene engineering technique is suitable for production of BDNF of same quality in a large scale.

Method for Production

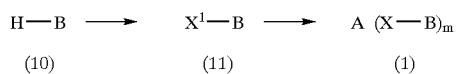

wherein A is a residue of a brain-derived neurotrophic factor, B is a residue of 1-acyl-glycerol derivative having a hydroxy group at the 2-position of the glycerol moiety, which is prepared by removing a hydrogen atom from the hydroxyl group, X is a chemical cross-linkage, m is an average number of the introduction, and is not less than about 0.5, and $X^1$ is a chemical cross-linkage having a reactive functional group.

The reactive functional group for $X^1$ means a functional group being activated so as to proceed the chemical cross-linking reaction with a functional group such as an amino group, a carboxyl group of BDNF. More particularly, the reactive functional group is, for example, a carboxyl group, an amino group, or an activated carboxyl group.

For compound (11) having a carboxyl group as a reactive functional group, the reactive functional group may be introduced by reacting a dicarboxylic acid anhydride having 2 carboxyl groups with a 1-acyl-glycerol derivative in an inert solvent in the presence of a catalyst, if necessary, in the presence of a base. The inert solvent includes, for example, aprotic solvents (e.g., dimethylformamide, acetonitrile, etc.), ethers (e.g., tetrahydrofuran, etc.), aromatic solvents (e.g., toluene, etc.), halogenated hydrocarbons (e.g., dichloromethane, dichloroethane, etc.), etc. The catalyst includes, for example, acids (e.g., p-toluenesulfonic acid, etc.), pyridines (e.g., 4-dimethylaminopyridine, 4-(N-pyrrolidyl)-pyridine, etc.). The base includes, for example, organic bases (e.g., triethylamine, pyridine, etc.). The reaction temperature is in the range of about 0° C. to about 100° C.

For compound (11) having an activated carboxyl group as a reactive functional group, the method for activation of a carboxyl group is, for example, mixed acid anhydride method, active ester method, etc. The mixed acid anhydride method is carried out by reacting a 1-acyl-glycerol derivative having a carboxyl group being introduced thereto obtained in the above method with an alkyloxycarbonyl halide in an inert solvent in the presence of a base under non-aqueous conditions to give the compound (11). The alkyloxycarbonyl halide includes, for example, isobutyloxycarbonyl chloride, sec-butyloxycarbonyl chloride, isopropyloxycarbonyl chloride, ethyloxycarbonyl chloride, methyloxycarbonyl chloride, etc. The inert solvent may be aprotic solvents (e.g., dimethylformamide, acetonitrile, etc.), ethers (e.g., tetrahydrofuran, etc.), aromatic solvents (e.g., toluene, etc.), etc. The base may be alkylamines (e.g., triethylamine, N-methylmorpholine, etc.), pyridines (e.g., pyridine, 4-dimethylaminopyridine, 4-(N-pyrrolidinyl)pyridine, etc.), and a combination of these solvents. The reaction temperature is in the range of about −20° C. to about room temperature.

The active ester method is carried out by reacting a 1-acyl-glycerol derivative having a carboxyl group introduced thereto obtained in the above method and an N-hydroxyimide or a phenol in the presence of a condensing agent in an inert solvent in the presence of a base to give the compound (11). The N-hydroxyimide includes, for example, N-hydroxysunccinimide, etc. The phenol includes, for example, 4-nitro-phenol, pentachlorophenol, pentafluorophenol, 4-nitorthiophenol, etc. The condensing agent includes carbodiimides such as dicyclohexylcarbodiimide, 1-(3-dimethylamino)propyl)-3-ethyl-carbodiimide hydrochloride, etc. The inert solvent may be aprotic solvents (e.g., dimethyl-formamide, acetonitrile, etc.), ethers (e.g., tetrahydrofuran, etc.), aromatic solvents (e.g., toluene, etc.), halogenated hydrocarbons (e.g., dichloromethane, dichloroethane, etc.). The base may be, for example, alkylamines (e.g., triethylamine, etc.), pyridines (e.g., pyridine, 4-dimethylaminopyridine, 4-(N-pyrrolidyl)pyridine, etc.), or a combination of these solvents. The reation temperature is in the range of about 0° C. to about 100° C.

In case of using compound (11) having a carboxyl group as a reactive functional group, a BDNF (1) being modified with a 1-acyl-glycerol derivative can be prepared by reacting the compound (11) with BDNF using a condensing agent in a solvent in the presence of a base. The condensing agent includes carbodiimides such as dicyclohexyl-carbodiimide, 1-(3-dimethylamino)propyl)-3-ethyl-carbodiimide hydrochloride, etc., or a combination of these carbodiimides and an N-hydroxyimide such as N-hydroxysuccinimide, etc. The solvent is, for example, aprotic solvents (e.g., dimethylformamide, acetonitrile, etc.), ethers (e.g., tetrahydrofuran, etc.), or a mixed solvent of these solvents and water, and water, etc. The base may be, for example, alkylamines (e.g., triethylamine, etc.), pyridines (e.g., pyridine, 4-dimethylaminopyridine, 4-(N-pyrrolidyl) pyridine, etc.) and a combination thereof. The reaction temperature is in the range of about 0° C. to about 100° C.

In case of using compound (11) having an activated carboxyl group as a reactive functional group, a BDNF (1) being modified with a 1-acyl-glycerol derivative can be prepared by reacting the compound (11) with BDNF in an inert solvent in the presence of a base. The inert solvent is, for example, aprotic solvents (e.g., dimethylformamide, acetonitrile, etc.), ethers (e.g., tetrahydrofuran, etc.), or a mixed solvent of these solvents and water, and water, etc. The base may be, for example, alkylamines (e.g., triethylamine, etc.), pyridines (e.g., pyridine, 4-dimethylaminopyridine, 4-(N-pyrrolidyl)pyridine, etc.) and a combination thereof. The reaction temperature is in the range of about 0° C. to about 100° C.

In case of using compound (11) having an activated imide group as a reactive functional group, a BDNF (1) being modified with a 1-acyl-glycerol derivative can be prepared by reacting the compound (11) with BDNF in an inert solvent in the presence of a base. The inert solvent may be, for example, aprotic solvents (e.g., dimethylformamide, acetonitrile, etc.), ethers (e.g., tetrahydrofuran, etc.), a combination of water and these solvent, or water. The base includes, for example, alkylamines (e.g., triethylamine, etc.), pyridines (e.g., pyridine, 4-dimethylaminopyridine, 4-(N-pyrrolidyl)pyridine, etc.), or a combination of these solvents. The reaction temperature is in the range of about 0° C. to about 100° C.

The BDNF being modified with a 1-alkanoyl-glycerol derivative of the present invention which is obtained by the above method can be purified by one of the following methods or a combination thereof. (1) Polyethylenimine fractionation, (2) Gel filtration chromatography with Sephacryl S-200; (3) Ion exchange chromatography with Biorex-70 resin or CM Sephadex; (4) Ammonium sulfate fractionation and/or pH fractionation, and (5) Affinity chromatography using an antibody resin which is prepared from an antibody isolated from hybridomas or sensitized animals. The modified BDNF can be desorbed under acidic conditions or slightly denaturation conditions.

The exact dosage and the administration schedule of the brain-derived neurotrophic factor being modified with a 1-alkanoyl-glycerol derivative of the present invention should vary according to the dosage to be required for each patient, the method for treatment, kinds of diseases to be treated, or the degree of necessity, and further according to the diagnosis by a physician. When administered parenterally, the dosage and the frequency of the administration may vary according to the conditions, ages, body weights of patients, and administration routes, but when it is administered subcutaneously or intravenously in the form of an injection, then the daily dosage thereof is in the range of about 1 to about 2500 µg, preferably in the range of about 10 to about 500 µg, per 1 kg of the body weight in an adult. When it is administered to the air tract in the form of an aerosol spray, the daily dosage thereof is in the range of about 1 µg to about 2500 µg, preferably in the range of about 10 to about 500 µg, per 1 kg of the body weight in an adult. The administration schedule is either continuous daily administration, intermittent administration, or a schedule of combining these methods.

When administered orally, the dosage and the frequency of administration may vary according to the conditions, ages, body weights of patients, and administration routes, and the daily dosage thereof is in the range of about 5 to about 2500 µg, preferably in the range of about 10 to about 1000 µg per 1 kg of the body weight in an adult.

The present modified BDNF is locally administered to severed sensory neurons at one of the various tissues such as geniculate, pyramidal and nodule nerve ganglion; vestibular auditory nerve complex of the 8th cranial nerve; ventral posterolateral nucleus of maxillomandibular of trigeminal ganglion; and mesencephalic nucleus of trigeminal nerve. In this case, it is preferably administered by absorbing to a membrane being capable of transplating at neighborhood of said severed neurons, such as Silastic membrane.

The exact dosage and the administration schedule of the brain-derived neurotrophic factor being modified with a 1-alkanoyl-glycerol derivative of the present invention for a patient suffering from type 2 diabetes mellitus should vary according to the dosage to be required for each patient, the method for treatment, kinds of diseases to be treated, or the degree of necessity, and further according to the diagnosis by a physician. When administered parenterally, the dosage and the frequency of the administration may vary according to the conditions, ages, body weights of patients, and administration routes, but when it is administered subcutaneously or intravenously in the form of an injection, then the daily dosage thereof is in the range of about 1 to about 500 µg, preferably in the range of about 10 to about 250 µg, per 1 kg of the body weight in an adult. When it is administered to the air tract in the form of an aerosol spray, the daily dosage thereof is in the range of about 1 µg to about 500 µg, preferably in the range of about 10 to about 250 µg, per 1 kg of the body weight in an adult. The administration schedule is either continuous daily administration, intermittent administration, or a schedule of combining these methods.

A pharmaceutical composition can be prepared by mixing the brain-derived neurotrophic factor being modified with a 1-acyl-glycerol derivative of the present invention with a pharmaceutically acceptable non-toxic carrier. When a pharmaceutical composition for parenteral administration (subcutaneous injection, intramuscular injection, or intravenous injection) is prepared, it is preferably in the form of a solution preparation or a suspension preparation. When a pharmaceutical composition for intravaginal administration or rectal administration is prepared, it is preferably in the form of a semi-solid preparation such as cream or suppository. When a pharmaceutical composition for intranasal administration is prepared, it is preferably in the form of a powder, a nasal drop, or an aerosol.

The pharmaceutical composition is administered in the form of a single dosage unit, and can be prepared by any conventional method that is known in the pharmaceutical field such as methods disclosed in Remington's Pharmaceutical Science (published by Mack Publishing Company, Easton, Pa., 1970). An injection preparation may optionally contain as a pharmaceutical carrier a protein derived from plasma such as albumin, an amino acid such as glycine, or a carbohydrate such as mannitol, and additionally a buffering agent, a solubilizer, or an isotonic agent, etc. can be contained. When the present pharmaceutical composition is in the form of an aqueous solution preparation or a lyophilized preparation, it may preferably contain a surfactant such as Tween 80 (registered trade mark), Tween 20 (registered trade mark), etc. in order to avoid aggregation. When the present pharmaceutical composition is a composition for parenteral administration other than an injection preparation, then it may contain distilled water or physiological saline solution, polyalkylene glycol such as polyethylene glycol, an oil derived from plant, hydrogenated naphthalene, etc. For example, a pharmaceutical composition such as a suppository for intravaginal administration or rectal administration may contain as a conventional excipient polyalkylene glycol, vaseline, cacao butter, etc. A pharmaceutical composition for intravaginal administration may contain an absorbefacient such as a bile salt, an ethylenediamine salt, a citrate, etc. A pharmaceutical composition for inhalation may be in the form of a solid preparation, and may contain as an excipient lactose, etc., and a pharmaceutical composition for intranasal drop may be in the form of an aqueous solution or an oily solution.

The present pharmaceutical composition is especially preferable in the form of a formulation by which the present compound can persistently be given to a subject by a single administration for a long term, e.g., for one week to one year, and various sustained release preparations, depot preparations, or implant preparations can be employed.

The present BDNF being modified with a 1-acyl-glycerol derivative may be in the form of a pharmaceutically acceptable salt thereof having a low solubility in a living fluid. Such pharmaceutically acceptable salts are, for example, (1): an acid addition salt such as phosphate, sulfate, citrate, tartrate, tannate, pamoate, alginate, polyglutamate, naphthalenemono- or di-sulfonate, polygalacturonate, etc., (2): a salt or complex with a polyvalent metal cation such as zinc, calcium, bismuth, barium, nickel, etc, or a combination of (1) and (2), for example, a tannic acid-zinc salt, etc. The present BDNF being modified with a 1-acyl-glycerol derivative is preferably converted into a slightly-water-soluble salt thereof, which is mixed with a gel, for example, aluminum monostearate gel and sesame oil, etc. to give a suitable injection preparation. In this case, especially preferable salt is a zinc salt, a tannic acid-zinc salt, a pamoate, etc. Another type of a sustained release injection preparation is ones wherein the present BDNF being modified with a 1-acyl-glycerol derivative is preferably converted into a slightly-water-soluble salt thereof, which is further enclosed in a slow-disintegrative non-toxic and non-antigenic polymer such as a polymer or a copolymer of polylactic acid/polyglycolic acid. In this case, especially preferable salt is zinc salt, tannic acid-zinc salt, pamoate, etc. In addition, a neurotrophic factor or a slightly-water-soluble salt thereof can be enclosed into a cholesterol matrix or a collagen matrix to give a sustained release preparation.

The pharmaceutical preparation for oral administration may be ones which are prepared by microencapsulating the present BDNF being modified with a 1-acyl-glycerol derivative or a salt thereof with lecithin, cholesterol, a free fatty acid, or ones which are prepared by enclosing said microcapsules into gelatin capsules, or ones which are prepared by enclosing the BDNF being modified with a 1-acyl-glycerol derivative or a salt thereof in enteric capsules, etc. These preparations may additionally contain, for example, an absorbefacient, a stabilizer, a surfactant, etc.

Since lecithin, which is one of the 1-acyl-glycerol derivatives used for modifying BDNF of the present invention, is a non-toxic substance being widely and naturally existing, lecithin-modified BDNF is also safe from the viewpoint of toxicity.

EXAMPLES

Reference Example 1
Synthesis of 2-(4-hydroxycarbonylbutyroyl)lysolecithin:

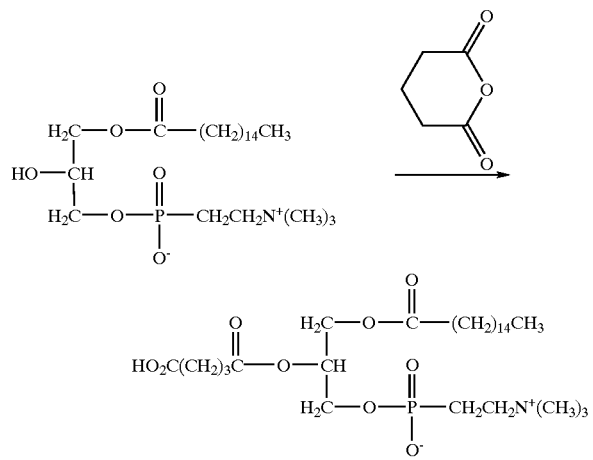

To a suspension of lysolecithin, which has a hydroxy group at the 2-position of the glycerol moiety (the acyl group $R^4$ of the formula (4) is palmitoyl group, hereinafter the same) (204 mg, 0.4 mmol) in chloroform-pyridine (8 ml/2 ml) were added DMAP (N,N-dimethylaminopyridine) (98 mg, 0.8 mmol) and glutaric anhydride (91 mg, 0.8 ml), and the mixture was stirred at 60° C. for 15 hours. The reaction solution was cooled and concentrated under reduced pressure. The concentrated residue was dissolved in chloroform/methanol/water=4:5:1 (2 ml), and the reaction solution was passed through the ion exchange column (Dowex 50W—X8), which had been equilibrated with said solution, concentrated under reduced pressure, and the residue was purified by silica gel column chromatography. Yield: 225 mg (0.36 mmol, 90%) $^1$H-HMR (CDCL$_3$): 0.84 (t, 3H), 1.20 (brs), 1.52–1.60 (brs, 2H), 1.80–1.95 (m, 2H), 2.20–2.42 (m, 6H), 3.35 (s, 9H), 3.78 (m, 4H), 3.90–4.35 (m, 4H), 5.20 (s, 1H)

Reference Example 2
Synthesis of an Active Ester of 2-(4-hydroxycarbonylbutyroyl)-lysolecithin:

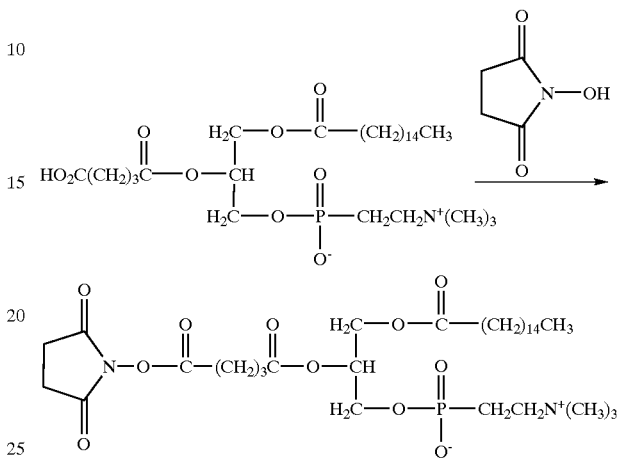

The carboxylic acid (225 mg, 0.36 mmol) obtained in Reference Example 1 was dissolved in dichloromethane (5 ml), and the mixture was cooled to 0° C., and thereto were added N-hydroxysuccinimide (41 mg, 0.36 mmol) and DCC (74 mg, 0.36 mmol). The mixture was stirred at room temperature for 15 hours. The insoluble materials are filtered through Celite, and the solvent was evaporated under reduced pressure to give an active ester.

Example 1

Water (5.4 ml) was added to a 30 mg/ml solution of r-h BDNF (1.7 ml), and the pH value of the solution was adjusted to pH 11 under water-cooling, and stirred. The aqueous solution (2.4 ml) of 0.6 equivalent of 2-O-(4-hydroxycarbonylbutyryl)lysophosphoryl choline hydroxysuccinimide ester to the whole amino groups of the r-h BDNF (recombinant human brain-derived neurotrophic factor) was added dropwise to the reaction mixture, and the mixture was stirred for 12 hours under water-cooling. The reaction solution was filtered through an ultra filtration membrane (cut off: molecular weight 10,000) to remove the unreacted agents and lower molecular weight substances. The solvent was displaced with a 10 mM phosphoric acid/potassium phosphate mixed solution to give a title compound. The average number of the introduction of the lecithin derivative into the r-h BDNF was measured by time-of-flight mass spectrometry (TOF-MALDI MS). The spectral patterns of r-h BDNF and the above compound are shown in FIG. 1.

Example 2

Water (0.7 ml) was added to a 30 mg/ml solution of r-h BDNF (0.25 ml), and the pH value of the solution was adjusted under water-cooling, and the whole volume was adjusted to 1.2 ml and then stirred. The aqueous solution (0.23 ml) of 2-0-(4-hydroxycarbonylbutyryl)-lysophosphoryl choline hydroxysuccinimide ester of an equivalent to the whole amino groups of the r-h BDNF (as shown in the following Table) was added dropwise to the reaction mixture, and the mixture was allowed to stand for 12 hours under water-cooling. The reaction solution was filtered through an ultra filtration membrane (cut off: molecular weight 10,000) to remove the unreacted agents and lower molecular weight substances. The solvent was displaced with a 10 mM phosphoric acid/potassium phosphate mixed solution to give a title compound. The average number of the introduction of the lecithin derivative into the r-h BDNF was measured by time-of-flight mass spectrometry (TOF-MALDI MS).

TABLE 1

|  | pH value of the reaction solution | Equivalents to the amino groups |
| --- | --- | --- |
| Compound 2 | 11 | 0.6 |
| Compound 3 | 11 | 0.6 |
| Compound 4 | 11 | 0.6 |
| Compound 5 | 11 | 0.6 |
| Compound 6 | 11 | 0.6 |
| Compound 7 | 11 | 1.5 |
| Compound 8 | 7 | 1.5 |

Example 3
Evaluation of Efficacy of BDNF and Lecithinized BDNF (Example 1) on Diabetes Mellitus, and Study of the Method for Administration and Dosage Thereof:
Materials and Methods for Experiments
(1) Test animals:
Male C57BL/Ks j-db/db Jcl mice (7 weeks old) were purchased from Clea Japan, Inc. After pre-feeding for 5 weeks, the animals were used in the experiment at 12 weeks old.
(2) Breeding conditions:
The mice were kept in a room being controlled at a temperature of 23±2° C. under a relative humidity of 55±10% with an illumination cycle of light on (8:00 to 20:00) and light off (20:00 to 8:00). During the pre-feeding and the experiment, the animals were given food (CE-2, Clea Japan, Inc.) and sterilized tap water ad libitum.
(3) Identification of individuals and cages
Each mouse was identified by writing the number thereof on the tail with oil-based ink. Cages were marked with a label wherein a name in charge of the experiment, the date of arrival, strain of mice, sex, and source were indicated. During the pre-bleeding, the mice were kept in 10 animals/cage. After the experiment started, each animal was kept separately in 1 animal/cage.
(4) Determination of dosage and grouping
The following groups were set with respect to the dosage of BDNF, and lecithinized BDNF.
1: BDNF 10 mg/kg/day (n=5)
2: BDNF 20 mg/kg/day (n=5)
3: Lecithinized BDNF 1 mg/kg/day (n=5)
4: Lecithinized BDNF 3 mg/kg/day (n=5)
5: Lecithinized BDNF 10 mg/kg/day (n=5)
6: Vehicle-treated group (n=5)
(5) Selection of hyperglycemic animals and grouping thereof
Five days prior to the administration, the mice were kept separately, and the amount of food consumption, body weight, blood glucose level were monitored until the administration day. The animal were grouped into 6 groups as indicated in the above (4) with respect to body weight and blood glucose level on the administration day, and the amount of food consumption (g/head/day) in a period from 5 days before the administration to the administration day. When grouping, mice having no hyperglycemia (300 mg/kg or less) and mice having apparently in bad conditions were excluded in the experiment.
(6) Preparation of dosing solution
The method for preparation is indicated below. The vehicle was 10 mM $KH_2PO_4/H_3PO_4$ (pH 3.0) containing 0.1% BSA, and the test 5 compound was diluted.

TABLE 2

| Groups | Concentration of dosing solution |
| --- | --- |
| BDNF 10 mg/kg/Day | BDNF 1.0 mg/ml |
| BDNF 20 mg/kg/Day | BDNF 2.0 mg/ml |
| Lecithinized BDNF 1 mg/kg/Day | Lecithinized BDNF 0.1 mg/ml |
| Lecithinized BDNF 3 mg/kg/Day | Lecithinized BDNF 0.3 mg/ml |
| Lecithinized BDNF 10 mg/kg/Day | Lecithinized BDNF 1.0 mg/ml |

Figure 2:
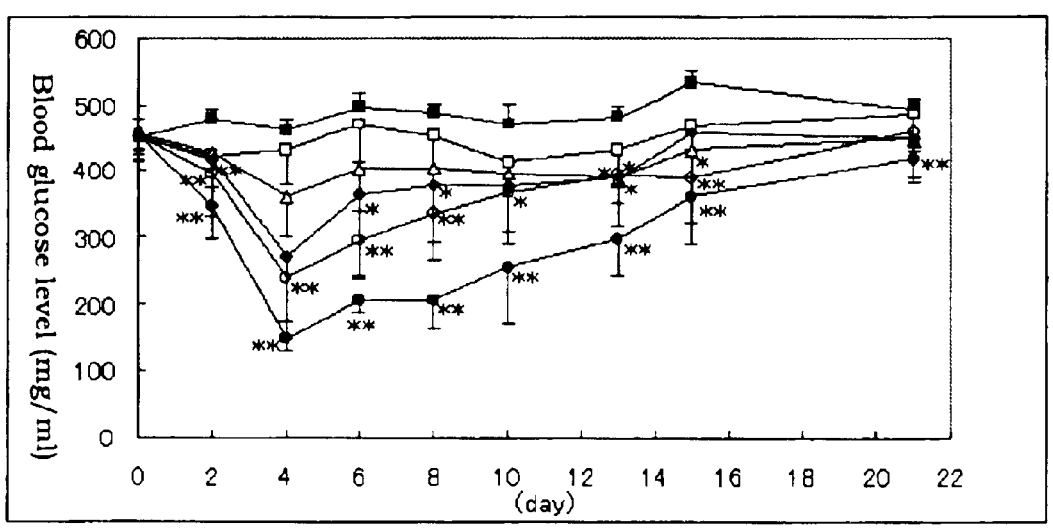
FIG. 2 is a graph showing the effects of the lecithinized BDNF and a BDNF on the blood glucose level of db/db mice.

(7) Administration method
The administration was carried out by subcutaneous administration on the back at a dose of 10 ml/kg for 5 days.
(8) Evaluation items
Every day during the administration period, and occasionally during the period after and before the administration, the body weight, the amount of food consumption and the blood glucose level were measured. The body weight and the amount of food consumption were measured with an automatic balance, and the blood glucose level was measured by Antosense II (Sankyo-Bayer) on the blood taken from the tail vein.
(9) Statistics Analysis
Dunnet's test was carried out on the body weight, the amount of food consumption, the blood glucose level, comparing with the data of the vehicle-treated group as control at each point by using statistical program SAS (registered trade name). The significant level was set at 5%.
(10) Results
The lecithinized BDNF or BDNF was subcutaneously administered to db/db mice during Day 0 to Day 4 (i.e., from the day of the beginning of the experiment to the 4th day). The blood glucose level during the administraion period and after the administration were measured with time-lapse, and the change of the blood glucose level is indicated in FIG. 2. In FIG. 2, ■ shows the data of the vehicle-treated group; □ shows the data of the BDNF 10 mg/kg treated group; Δ shows the data of the BDNF 20 mg/kg treated group; ♦ shows the data of the lecithinized BDNF 1 mg/kg treated group; ○ shows the data of the lecithinized BDNF 3 mg/kg treated group; ● shows the data of the lecithinized BDNF 10 mg/kg treated group; each data is expressed in the average ±S.D. (n=5); *:$P<0.05$,**:$P<0.01$ vs. the vehicle-treated group (Dunnett's test).

As is shown in said FIG. 2, the lecithinized BDNF showed remarkable dose-dependent hypoglycemic activity. Although BDNF showed dose-dependent hypoglycemic activity as well, there was no significant difference at the dose of 10 mg/kg. In addition, when comparing the data of the lecithinized BDNF 10 mg/kg treated group and the BDNF 10 mg/kg treated group, the lecithinized BDNF showed more potent effects.

Figure 3:
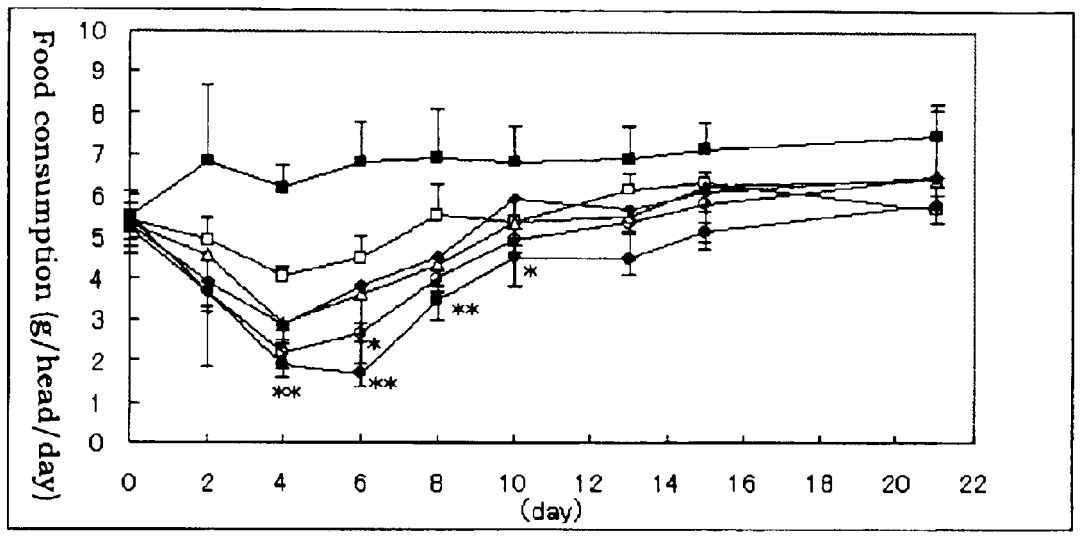
FIG. 3 is a graph showing the effects of the lecithinized BDNF and a BDNF on the amount of food consumption of db/db mice.

In addition, after subcutaneously administering a lecithinized BDNF and BDNF to db/db mice during the period of from Day 0 to Day 4, the amount of food consumption was measured during the administration period and after the administration with time-lapse, and the change of amount of food consumption is indicated in FIG. 3. In FIG. 3, ■ shows the data of the vehicle-treated group; □ shows the data of BDNF 10 mg/kg treated group; Δ shows the data of the BDNF 20 mg/kg treated group; ♦ shows the data of the lecithinized BDNF 1 mg/kg treated group; ○ shows the data of the lecithinized BDNF 3 mg/kg treated group; ● shows the data of the lecithinized BDNF 10 mg/kg treated group; each data is expressed in the average ±S.D. (n=5); *:P<0.05, **:P<0.01 vs. the vehicle-treated group (Dunnett's test).

Figure 4:
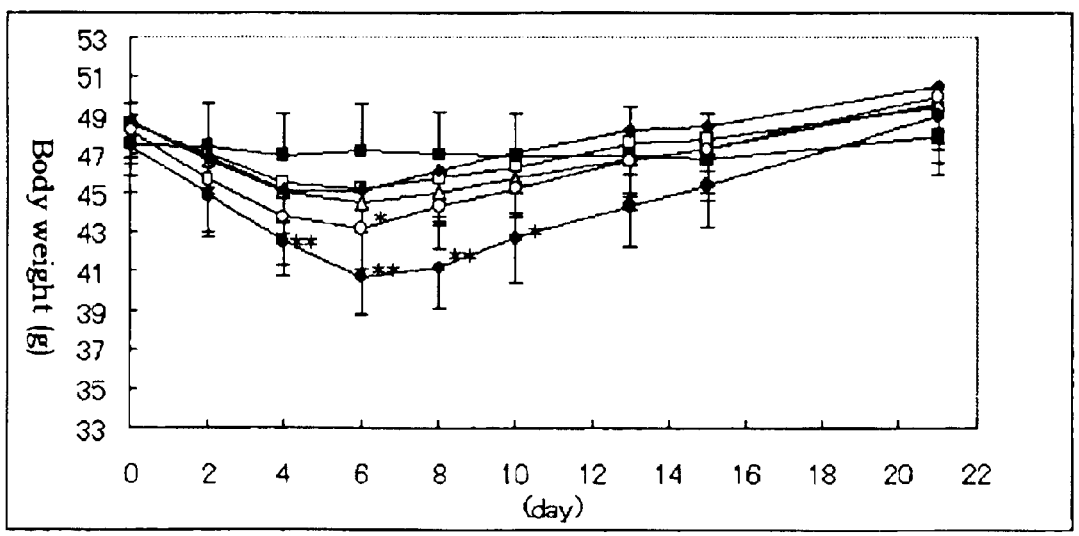
FIG. 4 is a graph showing the effects of the lecithinized brain-derived neurotrophic factor and a brain-derived neurotrophic factor on the body weights of db/db mice.

Further, after subcutaneously administering a lecithinized BDNF and BDNF to db/db mice during the period of from Day 0 to Day 4, the body weight was measured during the administration period and after the administration with time-lapse, and the change of the body weight is indicated in FIG. 4. In FIG. 4, ■ shows the data of the vehicle-treated group; □ shows the data of the BDNF 10 mg/kg treated group; Δ shows the data of the BDNF 20 mg/kg treated group; ♦ shows the data of the lecithinized BDNF 1 mg/kg treated group; ○ shows the data of the lecithinized BDNF 3 mg/kg treated group; ● shows the data of the lecithinized BDNF 10 mg/kg treated group; each data is expressed in the average ±S.D. (n=5); *:P<0.05, **:P<0.01 vs. the vehicle-treated group (Dunnett's test).

As is shown in FIG. 3 and FIG. 4, like the effects on the blood glucose level, the effects of lecithinized BDNF on the amount of food consumption and the body weight were dose-dependent and more remarkable than those of BDNF.

INDUSTRIAL APPLICABILITY

By modifying BDNF with a 1-acyl-glycerol derivative, there is obtained a modified BDNF having improved pharmacological activities, pharmacokinetics and the physical properties than BNDF. The BDNF being modified with a 1-acyl-glycerol derivative of the present invention is useful as a therapeutic agent for treatment of neurodegenerative diseases. In addition, the present modified BDNF exhibits dose-dependent hypoglycemic activity as well as an activity of promoting reduction of the amount of food consumption and the body weight, and hence, it is useful as a therapeutic agent for treatment of diabetes mellitus, especially type 2 diabetes mellitus.

What is claimed is:

1. A modified brain-derived neurotrophic factor comprising:
   a first moiety of a brain-derived neurotrophic factor, from which a number average of 1 to 10 hydroxyl group(s) and/or hydrogen atom(s) have been removed from the carboxyl groups and/or amino groups of amino acids of the brain-derived neurotrophic factor, and
   a second moiety that is a 1-acyl-glycerol derivative selected from the group consisting of 1-acyl-glycero-3-phosphoryl choline, 1-acyl-glycero-3-phosphoryl serine and 1-acyl-glycero-3-phosphoryl ethylamine;
   wherein said first and second moieties are chemically cross-linked.

2. A modified brain-derived neurotrophic factor, wherein said modified brain-derived neurotrophic factor is a compound of formula (1):

wherein A is a residue of a brain-derived neurotrophic factor,
   B is a residue of a 1-acyl-glycerol derivative having an oxygen atom at the 2-position of the glycerol moiety, which is prepared by removing a hydrogen atom from the hydroxyl group at the 2-position of the glycerol moiety,
   X is a chemical cross-linker, and
   m is number average of groups modifying the brain-derived neurotrophic factor and ranges from 1 to about 10.

3. The modified brain-derived neurotrophic factor according to claim 2, wherein X of the modified brain-derived neurotrophic factor is a group of the formula (2):

wherein $R^1$ is an alkylene group, or a group of the formula (3):

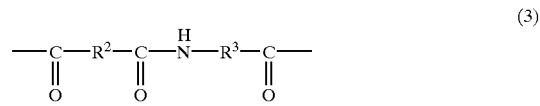

wherein $R^2$ and $R^3$ are independently an alkylene group.

4. The modified brain-derived neurotrophic factor according to claim 2, wherein the 1-acyl-glycerol derivative is 1-acyl-glycero-3-phosphoryl choline, 1-acyl-glycero-3-phosphoryl serine, or 1-acyl-glycero-3-phosphoryl ethylamine.

5. The modified brain-derived neurotrophic factor according to claim 2 or claim 3, wherein B of the modified brain-derived neurotrophic factor is a group of the formula (4):

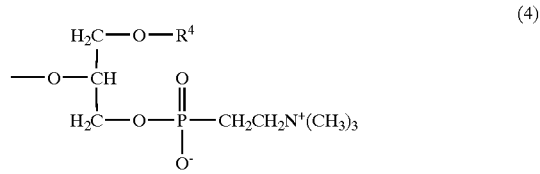

wherein $R^4$ is an acyl group.

6. The modified brain-derived neurotrophic factor according to claim 4, wherein the acyl group of formula (4) is an alkanoyl group having 8 to 30 carbon atoms.

7. A pharmaceutical composition comprising:
   a) a modified brain-derived neurotrophic factor of the formula (1):

wherein A is a residue of a brain-derived neurotrophic factor,
   B is a residue of a 1-acyl-glycerol derivative having an oxygen atom at the 2-position of the glycerol moiety, which is prepared by removing a hydrogen atom from the hydroxyl group at the 2-position of the glycerol moiety,
   X is a chemical cross-linker, and
   m is number average of groups modifying the brain-derived neurotrophic factor and ranges from 1 to about 10; and
   b) a pharmaceutically acceptable carrier.

8. The pharmaceutical composition according to claim 7, wherein X of the modified brain-derived neurotrophic factor is a group of the formula (2):

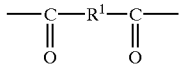
(2)

wherein $R^1$ is an alkylene group, or a group of the formula (3):

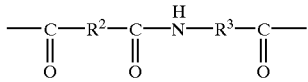
(3)

wherein $R^2$ and $R^3$ are independently an alkylene group.

9. The pharmaceutical composition according to claim 7, wherein the 1-acyl-glycerol derivative is 1-acyl-glycero-3-phosphoryl choline, 1-acyl-glycero-3-phosphoryl serine, or 1-acyl glycero-3-phosphoryl ethylamine.

10. The pharmaceutical composition according to claim 7 or claim 8, wherein B of the modified brain-derived neurotrophic factor is a group of the formula (4):

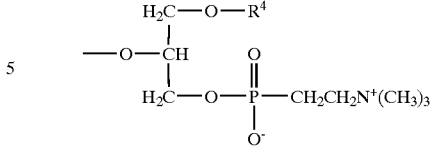
(4)

wherein $R^4$ is an acyl group.

11. The pharmaceutical composition according to claim 10, wherein the acyl group of formula (4) is an alkanoyl group having 8 to 30 carbon atoms.

12. A pharmaceutically acceptable salt of the modified brain-derived neurotrophic factor of claim 2.

13. The modified brain-derived neurotrophic factor according to claim 2, wherein the 1-acyl-glycerol derivative is lecithin.

* * * * *